United States Patent [19]
Belcour-Castro et al.

[11] Patent Number: 5,725,602
[45] Date of Patent: Mar. 10, 1998

[54] HAIR DYE COMPOSTION CONTAINING A PRODUCT OF GRINDING PLANTS OR PARTS OF PLANTS OF THE SPECIES IMPATIENS BALSAMINA, AND ITS APPLICATION

[75] Inventors: Béatrice Belcour-Castro, La Riche; Richard Martin, Roche Corbon, both of France

[73] Assignee: L'Oreal, Paris, France

[21] Appl. No.: 609,987

[22] Filed: Feb. 29, 1996

[30] Foreign Application Priority Data

Mar. 1, 1995 [FR] France .................. 95 02361

[51] Int. Cl.⁶ .................................................. A61K 7/13
[52] U.S. Cl. .................................................. 8/405
[58] Field of Search ............. 8/405, 438, 637.1; 424/195.1

[56] References Cited

U.S. PATENT DOCUMENTS 4,358,286 11/1982 Grollier et al. .................. 8/438
5,042,989 8/1991 Eck .................................. 8/438

FOREIGN PATENT DOCUMENTS 124 393 11/1984 European Pat. Off. .
94-2793 4/1994 Rep. of Korea .

OTHER PUBLICATIONS

English language translation of KR 942793, Pacific Chemical Co., Ltd., pp. 1–8, Apr. 1994.
Fairchild's Dictionary of Textiles, Fairchild Publications, Inc., p. 645, "wool" entry, 1959 No month available.
Chemical Abstract, 90:88642, M.A. Mikailov et al., "Balsam culture as valuable dye" (1978), 34(8), 72–5. No month available.
Chemical Abstract, 115:73525, Rama S. Jahan et al., "Balsam flowers, useful in wool dyeing & coloring" (1991), 38(1), 48–9. No month available.
Chemical Abstract, 79:170369, M. Thakur et al., "Anthocyanin pigmentation in roots of impatiens-SSP" & Can J Bot 56 (22), 1978, 2898–2903. No month available.
Biotechnol. Prog. 1993, vol. 9 No. 1, Topical Paper 7536, "Utilization of Hairy Root Cultures for Productions of Secondary Metabolites", Leena Toivonen.

Primary Examiner—Paul Lieberman
Assistant Examiner—Caroline L. Dusheck
Attorney, Agent, or Firm—Oliff & Berridge

[57] ABSTRACT

Hair dye composition including, as dyeing agent, a product of grinding, in particular a ground freeze-dried product, plants or parts of plants of the species *Impatiens balsamina*. This product of grinding is applied to hair in the form of a dispersion in a liquid, the said dispersion having a consistency that is sufficient to coat the hair. After a sufficient period of application the hair is rinsed to remove the composition.

14 Claims, No Drawings

HAIR DYE COMPOSTION CONTAINING A PRODUCT OF GRINDING PLANTS OR PARTS OF PLANTS OF THE SPECIES IMPATIENS BALSAMINA, AND ITS APPLICATION

BACKGROUND OF THE INVENTION

The invention relates to a hair dye composition and to a process for dyeing hair with the aid of such a composition.

More precisely, the invention relates to a dye composition including, as dyeing agent, a product of grinding at least one organ of the plant species *Impatiens balsamina*.

Many dyes are at present employed for dyeing hair, the majority of which are of synthetic origin, which are either direct dyes or oxidation dyes (whose colouring ability is developed only in the presence of an oxidizing agent).

The application of synthetic dyes can give rise to allergy phenomena in some people. It is quite obvious that, in the case of these people, it is desirable to avoid the use of such synthetic dyes.

This is one of the reasons why dye products of vegetable origin, with which allergic reactions are rarer, are now seen to he greatly favoured.

One of the plant materials most widely employed for dyeing hair is henna powder, which is the result of grinding dried foliage of the plant *Lawsonia inermis*. However, the dyeing properties of henna vary especially as a function of the source of the plant or of the harvesting period.

SUMMARY OF THE INVENTION

It is therefore important to have access to dyeing materials of vegetable origin which have a uniform and easily reproducible dyeing ability.

It has now been found that the products of grinding at least one organ of the plant *Impatiens balsamina* constitute particularly advantageous dyeing agents, in particular when applied to hair in the form of a dispersion in a liquid carrier, the said dispersion being sufficiently thick to be capable of coating the hair and adhering thereto for the time needed for the colour to develop.

DETAILED DESCRIPTION OF PREFERRED EMBODIMENTS

The subject of the invention is therefore a hair dye composition, in powder form, including as dyeing agent a product of grinding plants or parts of plants of the species *Impatiens balsamina*. The product of grinding may be obtained in particular by starting with roots, foliage, flowers, aerial parts of the plant (that is to say the whole plant less the roots), or else by starting with the entire plant.

According to a particular embodiment the product of grinding is at least partially dehydrated, which facilitates its storage in particular.

The dyeing agent may be obtained especially by freeze-drying the plants or parts of plants, and grinding.

The compositions of the invention can be prepared especially in the form of dry powders, so as to be able to be stored well. For example, the plants or parts of plants (optionally pulverized beforehand) may be freeze-dried to obtain a product whose mass represents less than 10%, and in particular less than 5%, of the mass of initial fresh plants (or parts of plants) and then, if appropriate, the freeze-dried product obtained is ground.

The dimensions of the particles of ground product, whether freeze-dried or not, are, for example, of the order of 0.1 to 2000 µm, especially from 0.5 to 750 µm, and in particular from 1 to 500 µm.

The dye composition of the invention may, of course, contain other conventional ingredients or excipients such as thickening agents (for example gum, pectin, alginate), surface-active agents, antioxidants, penetrating agents, sequestering agents, perfumes, buffers or pH modifiers, dispersants, hair-treating agents or conditioners, film-forming agents, preserving agents and opacifying agents. These other ingredients are added in the form of powders or in the form of solutions for impregnating the product of grinding (for example solutions in a volatile solvent which is subsequently removed). The composition may also contain other dyeing agents and especially other vegetable dyeing agents, either in the form of extracts or in the form of powders originating from the grinding of plants or of parts of plants containing a dyeing agent. The product of grinding *Impatiens balsamina* generally represents from 2 to 100% of the total mass of the composition in powder form.

Some organs of *Impatiens balsamina*, especially the roots of this plant, can be easily grown in vitro. Conditions which make it possible to produce these cultures in vitro are given below in the experimental section. Thus, by employing uniform cultivation conditions determined beforehand by routine experiments, it is possible to obtain a dyeing agent which has uniform properties, whatever the preparation period.

For application to the hair, the composition of the invention is put into the form of a dispersion of the product of grinding in an appropriate liquid carrier, the said dispersion having a sufficient consistency to adhere to hair without running after application to the said hair.

A further subject of the invention is a process for dyeing hair, characterized in that it includes the stages consisting in:

a) obtaining a composition in the form of an aqueous dispersion containing a product of grinding plants or parts of plants of the species *Impatiens balsamina*, in an appropriate liquid carrier, the said dispersion having a sufficient consistency to coat the hair and to adhere thereto without running after the application to the said hair;

b) bringing the hair to be dyed into contact with a composition as obtained in a) above;

c) and maintaining the said contact for a sufficient time to obtain the desired colour.

The aqueous dispersion obtained in stage a) above is applied in the form of a poultice coating the hair. The weight proportion of the dyeing material (product of grinding), as weight of dry material, is generally within the range from 1 to 50%, in particular from 3 to 40%, by weight relative to the total weight of the composition. If desired, the consistency of the composition may be increased by addition of a conventional thickening agent such as a gum, a pectin, an alginate or the like. The ready-for-use composition generally has a viscosity ranging from 5 to 45 poises, for example from 8 to 35 poises. The liquid carrier employed for obtaining the ready-for-use composition is an aqueous carrier, especially water or a mixture of water and of a solvent which is compatible with the application to hair and to the scalp (for example a lower alcohol like ethanol).

Excipients or adjuvants which are conventional in hair-care cosmetology, such as, for example, pH modifiers, hair-treatment agents or conditioners, wetting agents, thickening agents and the like, may additionally be added to the composition at the time of use. The pH of the aqueous dispersion, when ready for use, is generally between 2.5 and 12, preferably between 3 and 10.5.

The contact time between the dye composition of the invention and the hair depends especially on the initial colour of the hair and the shade which it is desired to impart to it. The contact times may be determined systematically by simple routine experiments on samples of hair. They may vary, for example, from 5 minutes to 4 hours, in particular between 15 minutes and 1 hour. The composition is applied to the hair, and conventional heating means may be applied, in order to work at a temperature not exceeding approximately 45° C. It is also possible to work without any heating means, at ambient temperature, or else with slightly warmed water.

After the desired contact time the hair is rinsed so as to remove especially the solid residues of the applied composition.

On white hair, the dye composition of the invention provides, in the case of a product of grinding roots of *Impatiens balsamina*, a coppery blond colour and, on blond hair, coppery highlights are obtained. With other parts of the plant it is possible to obtain various shades that can range, for example, from a medium yellowish brown to a rich brown (see the experimental section below).

The application of the compositions of the invention to volunteers has shown that these compositions do not have any irritant effect or allergic effect.

Moreover, colours obtained exhibit good behaviour and, in particular, stand up well to shampooing and to perspiration.

The following examples illustrate the invention.

EXAMPLE 1

Cultivation of Roots of *Impatiens Balsamina*

Pieces of leaves of *Impatiens balsamina* were cultured on a sterile agar gel medium (medium A), the composition of which will be given below, under the following conditions: leaves of *Impatiens balsamina* are immersed in an aqueous solution of calcium hypochlorite at a concentration of 40 g/l for 15 minutes in order to decontaminate them. The leaves are next rinsed by 4 successive treatments in sterile water. The leaves are next cut up into pieces of approximately 0.5 cm$^2$ and are then placed on medium A containing agar gel in a proportion of two pieces per dish. The cultures are kept in darkness at 26° C.

It is noted, uniformly, that some of these pieces of leaves give rise to root-hairs. These root-hairs have subsequently been transferred into sterile liquid medium A (without agar gel).

The roots thus obtained are maintained in this liquid medium, in the dark and with agitation (100 rotations/min) at a temperature of 26° C.

The pricking may be performed, for example, every fortnight. To do this, roots are withdrawn and regrown in order to inoculate, at a rate of 25 g/l, new medium A, this new medium being distributed beforehand into 250 ml conical flasks at a rate of 100 ml per flask and sterilized for 20 minutes at 115° C.

At the outcome of several maintenance cycles, some strains have exhibited a phenotype diversification displayed as the root colour: some of them appear to be coloured pink whereas, originally, the roots were pale yellow in colour. These roots have been separated and propagated. Various strains of roots of *Impatiens balsamina* have thus been obtained and, in particular, a strain Ib1 (not coloured pink) and Ib2 (which has a slight pink colour).

*Impatiens balsamina* roots originating from 2-week-old cultures were freeze-dried.

To do this, the root tissue is removed and freeze-dried after deep-freezing.

Approximately 1 g of freeze-dried product is obtained per 25 g of fresh material (roots).

The freeze-dried product is reduced to fine powder by grinding.

The particle size of the powder is of the order of 1 to 2 μm.

The medium A employed had the following composition:

| Constituents | Concentrations (mg l$^{-1}$) |
|---|---|
| $KNO_3$ | 1900.000 |
| $NH_4NO_3$ | 1650.000 |
| $KH_2PO_4$ | 170.000 |
| $MgSO_4.7H_2O$ | 370.000 |
| $CaCl_2.2H_2O$ | 440.000 |
| $MnSO_4.4H_2O$ | 22.300 |
| $H_3BO_3$ | 6.200 |
| $ZnSO_4.7H_2O$ | 8.600 |
| $Na_2MoO_4.2H_2O$ | 0.250 |
| $CuSO_4.5H_2O$ | 0.025 |
| $CoCl_2.6H_2O$ | 0.025 |
| KI | 0.830 |
| $FeSO_4.7H_2O$ | 27.850 |
| Mesoinositol | 100.000 |
| Nicotinic acid | 0.500 |
| Pyridoxine.HCl | 0.500 |
| Thiamine.HCl | 0.100 |
| L-glycine | 2.000 |
| $Na_2EDTA$ | 37.300 |
| Naphthylacetic acid (NAA) | 1.000 |
| Kinetin | 0.060 |
| Sucrose | 30000.0 |

The pH is adjusted to 5.8 before sterilization.

Agar at a concentration of 8 g/l is added in the case of the agar gel media A.

EXAMPLE 2

1.5 g of powdered freeze-dried product obtained in Example 1 are mixed with 10 ml of water to form a paste. The paste thus obtained is applied in the form of a poultice to half the length of a tress of white hair (on the root side of the hair).

The application is maintained for 3 hours 30 min at ambient temperature. The hair is next rinsed copiously with running water to remove the dye paste and is then dried.

With the powders originating from the strains Ib1 and Ib2, the hair thus treated has a blond colour with coppery highlights. The colour is uniform.

With some strains of root culture slight differences can be noticed in the colour shades obtained, with a pinker tone.

The same single established root culture gives products whose dyeing properties remain uniform on application to similar hair for a given time.

In other experiments the application to hair was maintained for 30 minutes instead of 3 hours 30 minutes. The intensity of the colour is then slightly lower.

Depending on the original colour of the hair, it is therefore possible to regulate the intensity of the colour to the desired degree as a function of the application time. The desirable contact times in order to obtain a particular desired shade can be determined beforehand by routine experiments performed on tresses of hair of diverse original colours.

EXAMPLE 3

*Impatiens balsamina* is grown from seed. The aerial parts are harvested and are reduced to powder with a grinder. A ground product is obtained with a mean particle size of approximately 0.5 mm.

The following composition is then prepared:

Ground product 20 g

Lukewarm water q.s. 100 g

Sodium hydroxide q.s. pH 9.5

This composition is applied to tresses of grey hair (containing 90% of white hair) at a temperature of 45° C. and the hair is kept at this temperature for 30 minutes and the hair is then rinsed with water and is dried.

A medium yellowish brown colour is obtained.

EXAMPLE 4

Products of grinding obtained from various parts of *Impatiens balsamina* were prepared as in Example 3 and then freeze-dried.

The following compositions were then prepared:

Ground freeze-dried product x grams

Lukewarm water (30° C.) q.s. 100 grams

Hydrochloric acid q.s. pH 5.5

The nature and the quantity of ground product and also the results of the dyeing operation (performed as described in Example 3) are shown below.

| Plant parts | Quantity of ground product in grams x = | Results |
| --- | --- | --- |
| Stems | 13.1 | Medium yellowish brown |
| Flowers | 7.9 | Medium yellowish brown |
| Foliage | 14.2 | Rich brown |
| Aerial parts | 11.6 | Rich yellowish brown |

EXAMPLE 5

20 ml of water and 3 g of ground freeze-dried product are mixed. The composition obtained is applied at ambient temperature to grey hair and the composition is left to act for one hour at ambient temperature (21° C.) and then the hair is rinsed and dried.

With a product of grinding flowers a fairly intense coppery blond colour is obtained.

With a product of grinding foliage a similar colour is obtained.

With a product of grinding roots a slightly golden blond colour is obtained.

EXAMPLE 6

Composition in Powder Form

The following composition is prepared:

Powdered foliage of *Impatiens balsamina* 55 g

Tragacanth 1 g

Pectin 1 g

Distearyldimethylammonium chloride 0.8 g

Trisodium citrate q.s. 100 g

At the time of use this composition is mixed with 1.5 times its weight of water at 38° C.

The mixture obtained is applied to light-blond hair and left in contact for 45 minutes. After rinsing, the hair exhibits an aesthetic coppery golden highlight.

We claim:

1. Hair dyeing process comprising the steps of:

a) obtaining a composition in the form of an aqueous dispersion containing a product of grinding plants or parts of plants of the species *Impatiens balsamina*, in an appropriate liquid carrier, said dispersion forming a pulp which has a consistency that is sufficient to coat the hair and to adhere thereto without running after the application to the hair;

b) bringing the hair to be dyed into contact with the composition as obtained in a) above;

c) and maintaining the said contact for a sufficient period to obtain the desired colour.

2. Process according to claim 1 wherein a contact time in said step b) is in a range of from 5 minutes to 4 hours.

3. Process according to claim 2, wherein said contact time is between 15 minutes and 1 hour.

4. Process according to claim 1, wherein the composition is contacted with the hair at a temperature not exceeding 45° C.

5. Hair dyeing process according to claim 1, wherein the process further comprises at least partially dehydrating the product of grinding.

6. Hair dyeing process according to claim 5, wherein a mass of the product of grinding represents less than 10% of a mass of the initial fresh plants or parts of fresh plants.

7. Hair dyeing process according to claim 1, wherein the process further comprises freeze drying the plants or parts of plants.

8. Hair dyeing process according to claim 1, wherein the parts of plants are selected from the group consisting of roots, foliage, flowers and aerial parts.

9. Hair dyeing process according to claim 1, wherein the process further comprises adding at least one of an excipient and a hair-treatment agent to the composition in a).

10. Hair dyeing process according to claim 9, wherein the excipient or hair-treatment agent is selected from the group consisting of thickening agents, surface-active agents, antioxidants, penetrating agents, buffers, dispersants, dyeing agents, film-forming agents, opacifying agents and perfumes.

11. Hair dyeing process according to claim 10, wherein the excipient or hair-treatment agent is added in the form of powder or in the form of a solution for impregnating the product of grinding.

12. Hair dyeing process according to claim 1, wherein the product of grinding has a particle size of the order of 0.1 to 2.000 μm.

13. Hair dyeing process according to claim 12, wherein the particle size is from 0.5 to 750 μm.

14. Hair dyeing process according to claim 12, wherein the particle size is from 1 to 500 μm.

* * * * *